United States Patent [19]

Borro

[11] Patent Number: 4,460,779

[45] Date of Patent: Jul. 17, 1984

[54] METHOD FOR PREPARING 2-LOWER ALKYL-SUBSTITUTED NAPHTHOXAZOLES BY WAY OF NON-TOXIC INTERMEDIATES

[75] Inventor: Giuliano Borro, Savona, Italy

[73] Assignee: Minnesota Mining & Manufacturing Company, St. Paul, Minn.

[21] Appl. No.: 193,380

[22] Filed: Oct. 2, 1980

[30] Foreign Application Priority Data

Oct. 9, 1979 [IT] Italy ................................. 50503 A/79

[51] Int. Cl.$^3$ ................... C07D 498/00; C07D 263/60
[52] U.S. Cl. ..................................... 548/217; 568/735
[58] Field of Search .......................................... 548/217

[56] References Cited

U.S. PATENT DOCUMENTS 3,653,943 4/1972 Kaempfen ........................... 548/217

OTHER PUBLICATIONS

Allan, A. W., et al., J. Chem. Soc. (c), 1397–1399, (1968).
Katritzky et al., "Advances in Heterocyclic Chemistry," vol. 17, pp. 130–131, (1974).
Selwitz, C. M., et al., J. Amer. Chem. soc., 77. pp. 5370–5373, (1955).
Elderfield, "Heterocyclic Compounds", vol. 5, pp. 314–317, John Wiley & Sons, Inc. New York.
Stein, C. W. C., et al., J. Amer. Chem. Soc., 64, pp. 2567–2569, (1942).
Morrison and Boyd, "Organic Chemistry," p. 1005, 3rd Ed. Allyn and Bacon, Inc., Boston, (1974).
Osman & Bassiuni, Journal of Organic Chemistry, vol. 27, (1962), 558.
Buehler & Pearson, Survey of Organic Synthesis, p. 417.

*Primary Examiner*—Donald G. Daus
*Assistant Examiner*—S. A. Gibson
*Attorney, Agent, or Firm*—D. M. Sell; J. A. Smith; Mark A. Litman

[57] ABSTRACT

The invention relates to a method for preparing 2-lower alkyl-substituted naphthoxazoles by way of non-toxic intermediates, and in particular relates to the preparation of a 2-lower alkyl-naphtho-[2,1-d]-oxazole or a 2-lower alkyl-naphtho-[1,2-d]-oxazole, which are of industrial interest in the field of cyanine dyes for use in photography, and in the field of optical brighteners for use in plastic materials. According to the invention, an aldehyde of a lower alkyl is reacted with 2-nitroso-1-naphthol or with 1-nitroso-2-naphthol, in the presence of a strong acid and a non-aqueous organic solvent, and the condensation product is then reduced.

10 Claims, No Drawings

METHOD FOR PREPARING 2-LOWER ALKYL-SUBSTITUTED NAPHTHOXAZOLES BY WAY OF NON-TOXIC INTERMEDIATES

DESCRIPTION

TECHNICAL FIELD

This invention relates to a method for preparing 2-lower alkyl-substituted naphthoxazoles by way of non-toxic intermediates.

BACKGROUND ART 2-alkyl-substituted naphthoxazoles (both [2,1-d] and [1,2-d] are prepared starting from hydroxynaphthylamine derivatives, which have been described as carcinogenic compounds.

Even though precautions can be taken to prevent any contact with such compounds during preparation of the 2-alkyl-substituted naphthoxazoles, it would be very desirable to find alternative methods. Naphthoxazoles are of industrial interest, for example in the field of cyanine dyes for photographic use, and in the field of optical brightners for use in plastic materials, and it is therefore necessary to seek preparations which are not dangerous.

As stated in "Advances in Heterocyclic Compounds", volume 17, edited by A. R. Katritzky and A. J. Boulton, University of E. Anglia, certain monozimes of the o-quinones can be reacted with benzaldehyde to give a compound which is reduced to certain oxazole compounds. However, it has been found that this method is not of general application, probably because the monoximes of the o-quinones give fused imidazoles if reacted with aliphatic aldehydes.

DISCLOSURE OF INVENTION

According to the present invention, it has been found that an aldehyde of a lower alkyl can be reacted with 2-nitroso-1-naphthol or 1-nitroso-2-naphthol to give a compound which can be reduced to a 2-lower alkyl-naphtho-[2,1-d]-oxazole or a 2-lower alkyl-naphtho-[1,2-d]-oxazole.

Consequently, the present invention relates to a method for preparing a 2-lower alkyl-naphtho-[2,1-d]-oxazole or a 2-lower alkyl-naphtho-[1,2-d]-oxazole, which consists substantially of condensing 2-nitroso-1-naphthol or 1-nitroso-2-naphthol with an aldehyde of a lower alkyl, and reducing the product thus obtained.

DETAILED DESCRIPTION OF THE INVENTION

Preferably, the present invention relates to the aforesaid method in which the condensation reaction is carried out in the presence of a strong acid or an organic solvent. According to one aspect, the present invention relates to the aforesaid method in which the condensation reaction is carried out in the presence of sulfuric acid in a non-aqueous organic solvent, said solvent preferably being dioxane. According to a further particular aspect, the present invention relates to the aforesaid method in which the condensation reaction is carried out in the presence of hydrochloric acid gas in a solution of acetic acid, preferably glacial acetic acid, to give a solution substantially free from water. According to an essential aspect, the present invention relates to a method as heretofore described, in which said aldehyde is an aliphatic aldehyde with a low R-CHO molecular weight, wherein R is a methyl, ethyl, propyl or isopropyl group, preferably a methyl or ethyl group, and more preferably a methyl group. The present invention also relates to a method as heretofore described, in which the condensation product is reduced by any means and preferably by adding a metal such as zinc or nickel directly to the solution of said product. Other metals or organic reducing agents may also be used, but are less desirable because of the additional effort needed to purify the final product. The expert of the art does not encounter any difficulty in the aforesaid reduction reaction, and can carry it out very simply by slowly adding a small quantity of zinc or nickel metal at a temperature of preferably 10° to 15° C. However, the condensation reaction can present some difficulty if carried out in the presence of sulfuric acid, as the yield is rather low unless the reaction is carried out in a non-aqueous organic solvent, preferably dioxane. The reaction temperature is preferably between 5° and 15° C., and more preferably about 10° C., and the order of addition is preferably such that the sulfuric acid is added to the dioxane, then the acetaldehyde and finally the nitrosonaphthol are added.

If hydrochloric acid is added in the form of the strong acid (which seems to be essential for the reaction), it should be added preferably in the form of anhydrous gas to the solution of the reagents (nitrosonaphthol and aldehyde), in particular at a temperature of below 25°–30° C., until the solution is saturated, the solvent being preferably acetic acid. The reaction yield is normally acceptable, even though the water has a negative effect, especially if the quantity of water present exceeds 10% (for this reason, it is preferable to use glacial acetic acid). It must be stated that the method of the present invention does not enable unsubstituted naphthoxazoles to be directly obtained, because an atom of chlorine enters (at least partly) the naphthalene ring as a substituent (in a position not properly defined). In particular, the only method for preparing the [2,1-d] naphthol derivative without substituents in the benzene nuclei, according to the present invention, appears to be to use sulfuric acid in the method of the present invention as heretofore described (in photography, this can be important, as 2-alkyl-naphthoxazole unsubstituted in the benzene nuclei is normally the most important compound of the series).

The corresponding naphthoxazoles can be obtained, if necessary, by using 2-nitroso-1-naphthol with certain substituents (for example 2-nitroso-1-naphthol substituted as follows: 4-chloro, 5-chloro, 7-chloro, 5,6-chloro, 5,8-dimethoxy, 6,8-dimethoxy, 6,7-dimethyl, 4-ethyl, 6-ethyl, 7-fluoro, 4-isopropyl, 4-isophenyl, 4-methoxy, 7-methoxy, 5-methoxy, 6-methoxy, 8-methoxy, 4-methyl, 6-methyl, 7-methyl or 5-pentyl). Similarly, 1-nitroso-2-naphthol with certain substituents can give the corresponding naphthoxazoles (using for example 1-nitroso-2-naphthoxazole substituted as follows: 4-bromo, 6-bromo, 8-bromo, 6-butyl, 4-chloro, 6-chloro, 8-chloro, 4,6-dibromo, 5,8-dibromo, 7,8-dimethoxy, 7,8-dimethyl, 6-isopropyl, 6-methoxy, 7-methoxy, 8-methoxy or 8-methyl).

The naphthoxazole prepared by the method of the present invention can be separated and isolated, as known, for example by pouring the reaction mixture (acid and substantially non-aqueous [i.e., less than 1% water]) in a large volume of water, alkalising it with a strong base (such as NaOH, HN$_4$OH or KOH) and extracting the compound (basic) with a non-aqueous solvent (such as ethyl ether, ligroin etc.), which is then dried and removed by distillation under reduced pressure.

The present invention is illustrated by the examples gives hereinafter.

EXAMPLE 1

2-methyl-naphtho-[2,1-d]-oxazole

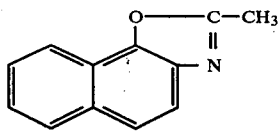

100 cc of concentrated sulfuric acid were added slowly to 800 cc of dioxane under stirring, the temperature being maintained at 7°-8° C. 88 g of acetaldehyde were dripped slowly into this solution, and then 143 g of 2-nitroso-1-naphthol were added in small quantities. Within 90 minutes, under stirring at 10° C., the solution dissolved and 84 g of powdered zinc were slowly added in very small quantities at this temperature, the temperature being kept less than 12° C. After the addition, stirring was continued for a further 3 hours, and the mixture was then left at ambient temperature overnight. The suspension was then poured into 4 liters of water and ice, also containing 400 cc of a 30% aqueous solution of sodium hydroxide. The suspension was extracted repeatedly, and dried overnight over anhydrous sodium sulphate. After filtering, the solvents were distilled off over a rotating evaporator. The residual oil was filtered under vacuum, and the fraction boiling at 155°-162° C./2 mm Hg was collected. 35 g of pure product were obtained in the form of a clear oil, which on standing solidified into a product having a M.P. of 37° C. The structure was confirmed by NMR and IR spectra.

|   | Percentage analysis | |
|---|---|---|
|   | Calculated | Found |
| C | 78.67% | 78.36% |
| H | 4.95% | 4.98% |
| N | 7.65% | 7.79% |

EXAMPLE 2

2-methyl-X-chloro-naphtho-[2,1-d]-oxazole

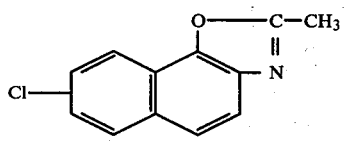

A suspension of 100 cc of glacial acetic acid, 100 cc of acetaldehyde and 200 g of 2-nitroso-1-naphthol was saturated with HCl under stirring, while maintaining the temperature below 25° C., to form a solution. 180 g of powdered zinc were added to this solution in very small quantities, while carefully maintaining the temperature below 15°-16° C. After the addition, the mixture was left stirring at ambient temperature overnight. The mixture was then poured under stirring into 5 liters of water and ice, made strongly basic with 2 liters of a 30% aqueous solution of sodium hydroxide. The mixture was then repeatedly extracted with ethyl ether, and the ether extracts were treated with activated carbon, filtered and dried over anhydrous sodium carbonate overnight. After filtering, the ether was distilled off, and the residual oil was distilled under vacuum, collecting the fraction boiling at 175°-185° C./2 mm Hg. On standing, the distilled oil became a white solid product. This product was further purified by recrystallization from ethanol, to give 110 g of white needles with a M.P. of 87° C. The structure was confirmed by IR and NMR spectra, but the position of the chlorine was not exactly determined.

|   | Percentage analysis | |
|---|---|---|
|   | Calculated | Found |
| C | 66.22% | 66.65% |
| H | 3.70% | 3.65% |
| N | 6.43% | 6.50% |
| Cl | 16.29% | 16.10% |

EXAMPLE 3

2-methyl-naphtho-[1,2-d]-oxazole

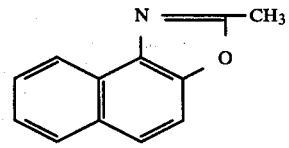

A suspension of 350 cc of glacial acetic acid, 25 cc of acetaldehyde and 50 g of 1-nitroso-2-naphthol was saturated with HCl gas under stirring, while maintaining the temperature below 25° C. A clear solution was obtained.

50 g of powdered zinc were added to this solution in small quantities while maintaining the temperature below 15°-16° C. After the addition, the mixture was left stirring at ambient temperature overnight. The mixture was then poured into three liters of water and ice made strongly basic with a 30% aqueous solution of sodium hydroxide. The mixture was then extracted repeatedly with ethyl ether, and the ether extracts were treated with activated carbon, filtered and dried overnight over anhydrous calcium chloride. After filtering, the ethyl ether was distilled off over a rotating evaporator, and the residual oil was distilled under vacuum, collecting the fraction boiling at 145°-155° C./2 mm of Hg. 26.5 g of yellow oil were obtained. The structure was confirmed by IR and NMR spectra.

|   | Percentage analysis | |
|---|---|---|
|   | Calculated | Found |
| C | 78.67% | 77.96% |
| H | 4.95% | 4.93% |
| N | 7.65% | 7.61% |

What is claimed is:

1. A method for preparing an alkyl-naphtho-[2,1-d]-oxazole or an alkyl-naphtho-[1,2-d]-oxazole wherein said alkyl is selected from the group consisting of alkyls having one, two, or three carbon atoms, said method comprising condensing 2-nitroso-1-naphthol or 1-nitroso-2-naphthol with an aldehyde of an alkyl having 1 to 3 carbon atoms and then reducing the resulting condensation product.

2. A method as claimed in claim 1, wherein the condensation reaction is carried out in the presence of a strong acid and an organic solvent.

3. A method as claimed in claim 2, wherein said strong acid is sulfuric acid, and said organic solvent is substantially non-aqueous.

4. A method as claimed in claims 1, 2 or 3, wherein the condensation reaction is carried out substantially in the absence of water.

5. A method as claimed in claims 2 or 3, wherein the condensation product is reduced by adding zinc or nickel metal to the obtained solution of said product.

6. A method as claimed in claims 1, 2 or 3, wherein the organic solvent is anhydrous dioxane.

7. A method as claimed in claims 1 or 2, wherein said strong acid is hydrochloric acid gas, and said organic solvent is acetic acid.

8. A method as claimed in claim 1, wherein said aldehyde is acetaldehyde.

9. A method as claimed in claim 4, wherein said aldehyde is acetaldehyde.

10. The method of claim 1 wherein the alkyl of said alkyl-naphtho-[2,1-d]-oxazole or said alkyl-naphtho-[1,2-d]-oxazole is selected from the group consisting of methyl, ethyl, propyl and isopropyl.

* * * * *